United States Patent [19]

Wieringa et al.

[11] Patent Number: 4,564,698

[45] Date of Patent: Jan. 14, 1986

[54] BIOLOGICALLY-ACTIVE TRICYCLIC AMINES

[75] Inventors: Johannes H. Wieringa, Heesch; Frans A. van der Vlugt, Oss, both of Netherlands

[73] Assignee: Akzo N.V., Arnhem, Netherlands

[21] Appl. No.: 460,259

[22] Filed: Jan. 24, 1983

Related U.S. Application Data

[63] Continuation of Ser. No. 268,330, May 29, 1981, abandoned.

[30] Foreign Application Priority Data

May 30, 1980 [NL] Netherlands ............... 8003141

[51] Int. Cl.$^4$ ............. C07C 69/76; C07C 87/28
[52] U.S. Cl. .................... 560/109; 514/227;
514/255; 514/325; 514/396; 514/427; 514/464;
514/533; 514/554; 514/649; 514/656; 544/154;
544/380; 544/381; 546/195; 546/248; 548/346;
548/347; 548/565; 548/579; 549/432; 560/58;
560/64; 560/103; 560/105; 560/107; 560/110;
564/180; 564/217; 564/265; 564/375; 564/387;
564/426
[58] Field of Search ............ 564/387, 375, 426, 329;
549/432; 424/316, 338

[56] References Cited

U.S. PATENT DOCUMENTS

| | | | |
|---|---|---|---|
| 3,732,299 | 5/1973 | Levine et al. | 564/387 X |
| 3,763,233 | 10/1973 | Houlihan et al. | 564/426 X |
| 3,912,781 | 10/1975 | Finger et al. | 564/426 X |
| 3,950,425 | 4/1976 | Burg et al. | 564/426 X |

FOREIGN PATENT DOCUMENTS 2252945  5/1974  Fed. Rep. of Germany ...... 564/426

*Primary Examiner*—Robert V. Hines
*Attorney, Agent, or Firm*—Abelman Frayne Rezac & Schwab

[57] ABSTRACT

The present invention relates to new tricyclic compounds of the formula:

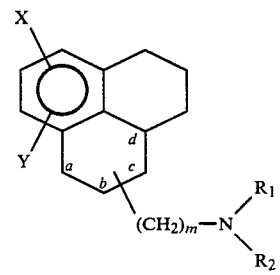

having valuable CNS and cardiovascular properties.

3 Claims, No Drawings

BIOLOGICALLY-ACTIVE TRICYCLIC AMINES

This is a continuation of application Ser. No. 268,330 filed May 29, 1981, and now abandoned.

The present invention relates to new biologically active tricyclic compounds, to methods for preparing these compounds and to pharmaceutical preparations containing these compounds as the active principle.

In particular the invention relates to tricyclic compounds having the general formula:

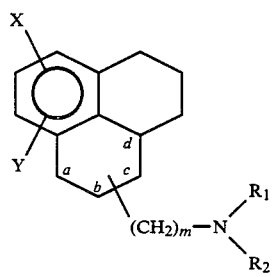

I or an acid addition salt thereof, whereby the substituent —$(CH_2)_m$—$NR_1R_2$ is present at one of the positions a, b or c, X and Y each represent hydrogen, alkyl (1–6 C), alkoxy (1–6 C), halogen, hydroxy, acyloxy, or both X and Y at vinical positions may also represent a methylene dioxy group, $R_1$ and $R_2$ represent hydrogen or alkyl (1–6 C) or $R_1 + R_2$ together with the nitrogen represent a heterocyclic 5- or 6-ring, which optionally may contain a second nitrogen atom or an oxygen atom, and m represents the number 0 or 1.

By alkyl group is meant a saturated alkyl group with 1–6 carbon atoms, such as methyl, ethyl, propyl, isopropyl, butyl, isobutyl, tertiary butyl, pentyl and hexyl.

The alkoxy group is an alkyloxy group in which the alkyl group is defined in the same way as above.

By "acyloxy" in the definition of X and Y is meant a

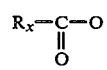

group in which $R_x$ represents an alkyl, phenyl or a phenylalkyl group, wherein the phenyl group may be substituted by one or more hydroxy, alkoxy or halogen groups.

By the heterocyclic 5- or 6-ring in the definition of $R_1 + R_2$ is meant a saturated or unsaturated 5- or 6-membered ring, such as pyrrole, pyrroline, pyrrolidine, piperidine, imidazole, imidazoline, imidazolidine, pyrazolidine, morpholine, piperazine, N-methyl piperazine and N-phenyl piperazine.

The compounds of the general formula I are prepared in a manner customarily employed for such compounds.

A general method of preparation is starting from a carboxylic acid of the general formula:

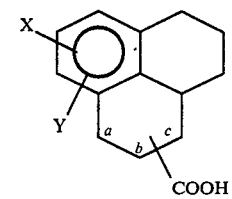

II or a lower aliphatic ester, anhydride or halide thereof, wherein the carboxylic acid group is present in one of the positions a, b or c and X and Y have the meanings specified above.

Compounds I, in which m=1, are prepared from these intermediates of formula II by reaction of said acid, ester, anhydride or halide with the compound:

III in which $R_1$ and $R_2$ have the above-mentioned meanings. The amide thus obtained is reduced in the usual manner, e.g. by a metal hydride, such as lithium aluminium hydride, to give a compound I in which m=1.

Compounds I where m=0 are prepared from the starting product II by means of one of the well-known rearrangements according to Hofmann, Curtius or Lossen. In these cases the compound II is converted via primary amides, azide or hydroxamic acid into the corresponding isocyanate having formula IV:

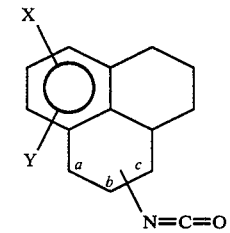

IV which subsequently is converted by hydrolysis into the primary amine I (where m=0).

Other preparation-methods start from a compound of the general formula V

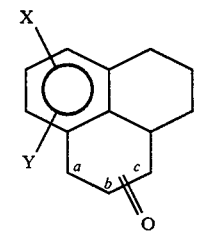

V where the oxo group is present at one of the locations a, b or c and X and Y have the above-mentioned meanings.

Starting with the compound of formula V the compounds of the invention with m=0 can be directly prepared by reductive aminetion. Thus, the ketone V reacts with formamide, alkylformamide, dialkylformamide or with an amine of formula III in the presence of a reducing agent such as formic acid, a metalhydride such as LiAlH₄, NaBH₄ or Na(CN)BH₃, or hydrogen in the presence of a catalyst such as platinum or palladium on carbon.

Furthermore compounds I, with m=0, may be prepared by reduction of the oxime having the formula:

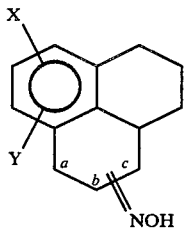

VI where the oxime group is present at one of the locations a, b or c.

Reduction of the oxime VI in the manner usually employed for an oxime e.g. with lithium aluminium hydride, with sodium or sodium amalgam in alcohol, or by means of catalytic hydrogenation, supplies the corresponding primary amine of formula I.

By reducing the ketone V using for example metalhydrides such as lithium aluminiumhydride or sodium boronhydride, the corresponding alcohol is obtained in good yield. The hydroxy group of this alcohol can be converted in the usual manner into a "leaving group", e.g. by means of tosylation, mesylation or halogenation, resulting in a compound of the general formula:

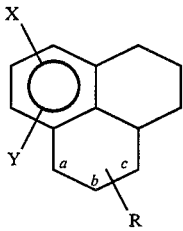

VII where R represents a "leaving group" and is present at one of the positions a, b or c and X and Y have the above-mentioned significance. Preferably the meaning of R in formula VII is halogen or sulphonyloxy group such as tosyloxy or mesyloxy.

This starting product of formula VII may be employed for the manufacture of compounds I in various ways.

Compounds I with m=0 can be obtained by condensation of compound VII with an amine of formula III or an acid salt of addition thereof. Furthermore compounds I with m=0 and R₁ and R₂ represent hydrogen, can be obtained by reaction of the compound VII with an alkali metal azide followed by reduction of the azide obtained into the corresponding primary amine in a manner customarily employed for the reduction of an azide, e.g. using diborane, via hydrogenation with Raney nickel or palladium as catalyst, or with metalhydrides such as LiAlH₄ or NaBH₄.

Compounds I, with m=1 and R₁ and R₂ represent hydrogen, can be obtained by reaction of the compound VII with an alkali metal cyanide followed by reduction of the nitrile thus obtained. The nitrile group is preferably reduced with the aid of lithiumaluminiumhydride.

A further method for producing compounds I, where the amino (methyl) substituent is present in position b, may start from the ketone V, in which the oxo group is present at position a.

If the ketone V (with oxo at position a)

is either halogenated, preferably brominated, and the resulting halide is allowed to react with an amine of formula III, or is reacted consecutively with hydroxylamine, tosylchloride and a strong base (Neber reaction), or is reacted consecutively with a strong base and a nitrite, followed by reduction of the oxime group, or is reacted with ammonia or a primary or secondary amine and (para) formaldehyde (Mannich reaction), a compound is obtained with the general formula:

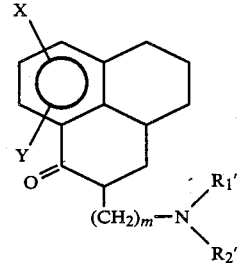

VIII where X, Y and m have the above-mentioned meanings and $R_1'$ and $R_2'$ have the same meaning as $R_1$ and $R_2$, but can also represent a N-protective group.

The compounds VIII are converted into the corresponding compound of formula I, by reduction of the keto group to a CH₂ group. This reduction is carried out in the usual manner, e.g. by means of catalytic hydrogenation or by means of Wolff-Kishner or Clemmensen reduction, or by hydrogenolysis of the corresponding dialkylthio-acetal, if required followed by splitting off the protective group.

Amines of the general formula III, which can be used in the above-mentioned methods of preparation, are for example: ammonia, methylamine, dimethylamine, ethylamine, diethylamine, isopropylamine, propylamine, dipropylamine, butylamine, dibutylamine, tert. butylamine, pyrrole, pyrroline, pyrrolidine, piperidine, imidazole, imidazoline, imidazolidine, pyrazolidine, piperazine, morpholine, N-alkylpiperazines and N-phenylpiperazine.

The compounds of formula I contain 2 chiral carbons (position d and the location where the amino-(methyl) group is attached to the ring), so that 2 racemates (one cis-racemate and one trans-racemate) and four optically active compounds I are possible. These different stereo isomers and enantiomers all belong to the compounds of this invention. The cis and the trans-compounds I can be separated in the usual way by fractionated crystallisation, column chromatography, preparative thin-layer chromatography, or partition chromatography. A racemate I can be resolved as usual into the optical antipodes, e.g. with the aid of an optically active acid.

The acid addition salts of the compounds of the invention are prepared in the usual way by reacting the free base I with an acid such as HCl, HBr or HI, phosphoric acid, tartaric acid, citric acid, ascorbic acid or salicyclic acid.

It is of course possible to convert one compound of the invention into another compound of the present invention.

Thus, for example, the non-substituted or mono-substituted (at the nitrogen atom) amine of formula I ($R_1$ and/or $R_2$=H) can be alkylated in the usual manner, e.g. by reaction with an alkylhalide. However it is more usual for this purpose to acylate the relevant nitrogen atom and subsequently to reduce the resulting N-acyl compound. For introducing methyl groups to the nitrogen atom preference is given to the procedure in accordance with Eschweiler-Clarke (reaction with formaldehyde and formic acid) or to the reaction with formaldehyde and sodiumcyanoborohydride in a suitable solvent, e.g. acetonitrile.

Furthermore it is possible to hydrolyse an alkoxy substituent and preferably a methoxy substituent at the phenyl group to the corresponding hydroxy group in a generally known manner e.g. with the aid of an acid, such as $BBr_3$ or HBr.

In turn this hydroxy group can be subsequently converted into an acyloxy group in the usual manner reacting it with the desired carboxylic acid or acid halide, anhydride or reactive ester thereof.

The compounds of the invention exhibit CNS and cardiovascular properties.

In view of their activity in some CNS-tests, the compounds of the invention may be used e.g. in the treatment of depression.

The compounds show furthermore effects on heart rhythm, which may be indicative for potential antiarrhythmic activity.

The compounds of the present invention, and particularly the compounds with a dihydroxy or dialkoxy substitution pattern at positions 4,5 or 5,6 (for the numbering employed see page 9) of the basic skeleton furthermore exhibit a stimulating effect on the dopamine receptors, so that inter alia they are suitable for the prophylactic treatment of a heart infarction, for reducing blood pressure, and especially for the treatment of patients suffering from Parkinsons disease; they furthermore induce suppression of prolactin secretions.

Compounds I can be administered either enterally or parenterally.

Mixed with suitable carriers they can be brought into a form suitable for oral administration such as pills, tablets and capsules. For injection purposes the compounds are dissolved, emulsified or suspended in a liquid suitable for injection. The compounds concerned can furthermore be administered in the form of a suppository or spray.

The compounds I are preferably administered in a dosage of 0.01 mg up to 10 mg per kg bodyweight per day. For human use a dosage between 1 and 500 mg per day is recommended.

The following nomenclature and numbering have been used in the examples:

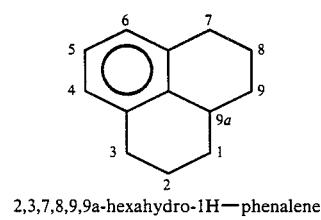

2,3,7,8,9,9a-hexahydro-1H—phenalene

EXAMPLE 1

2,3,7,8,9,9a-hexahydro-6-methoxy-N-methyl-1H-phenalene-1-amine.HCl (a) 2,3,7,8,9,9a-hexahydro-6-methoxy-1H-phenalene-1-on A tetrahydrofurane (THF) solution of 1.34 g lithium diisopropylamine was added dropwise during stirring to a THF solution of 1.23 g 2,3,7,8,9,9a-hexahydro-6-methoxy-1H-phenalene-1-carboxylic acid. After stirring for 3 hours the solution was cooled to −78° C. and added dropwise to an ether solution to which oxygen was added. The take-up of oxygen was quantitative. The reaction mixture was decanted, evaporated in vacuo to about 5 ml, diluted with ether and poured into 4 n HCl.

Extraction with ether followed by drying over magnesium sulphate and evaporation of the solvent gave a residue (α-hydroperoxy acid), which was dissolved in methylene chloride. A solution of four equivalents N,N-dimethylformamide dimethylacetal in methylene chloride was added dropwise to this solution at −78° C. under $N_2$. The resultant solution was stirred at room temperature until the iodine-starch test for peroxides was negative. Methylene chloride was subsequently evaporated and the residue was purified by means of column chromatography. Yield: 0.64 gram (60%) oil.

(b) cis-2,3,7,8,9,9a-hexahydro-6-methoxy-N-methyl-1H-phenalene-1-amine.HCl 1.55 g Methylamine.HCl and 2.3 g mol. sieve 4A was added to 4.97 g of the 1-keto compound obtained in (A), dissolved in 45 ml methanol. The mixture was subsequently stirred for 24 hours at room temperature, after which 1.45 g of sodium-cyanoborohydride was added. Then stirring was carried out once more for 24 hours at room temperature and then successively the reaction mixture was concentrated, the residue was stirred with 25 ml 4 n NaOH and extracted with 3×25 ml methylene sulphate and the organic extracts dried and concentrated, and subsequently the residue was dissolved in 5 ml ethanol. Then 5.5 ml of 4.38 n HCl in ethanol and 50 ml dry ether were added to this solution. The precipitate obtained was filtered off and re-crystallised from ethanol-ether.

Yield: 4.6 g (75%). Melting point: 221°–225° C. Rf in methanol:acetic acid (98:2)=0.4 on $SiO_2$. The compound obtained turned out to possess the cis configuration.

Chromatographic separation of the mother liquor (see Example 5) also supplied a small quantity of trans-compound.

EXAMPLE 2

In an analogous manner to that described in Example 1(b) the following compounds were prepared:
cis 2,3,7,8,9,9a-hexahydro-N-methyl-1H-phenalene-1-amine.HCl prepared; melting point 195°–200° C.;
cis 2,3,7,8,9,9a-hexahydro-5,6-dimethoxy-N-methyl-1H-phenalene-1-amine.HCl; melting point 182°–189° C.; and the corresponding trans isomer, melting point 189°–190° C.;
cis 2,3,7,8,9,9a-hexahydro-5-methoxy-N-methyl-1H-phenalene-1-amine.HCl, melting point 219° C.;
cis 2,3,7,8,9,9a-hexahydro-6-chloro-N-methyl-1H-phenalene-1-amine.HCl, melting point 219°–220° C.

By replacing the methylamine.HCl as used in Example 1(b) by other amines the following compounds were produced:

cis 2,3,7,8,9,9a-hexahydro-N-isopropyl-1H-phenalene-1-amine.tartrate; melting point 154°-156° C.;

cis 2,3,7,8,9,9a-hexahydro-N,N-diethyl-1H-phenalene-1-amine.HCl; melting point 188°-191° C.;

cis 2,3,7,8,9,9a-hexahydro-6-methoxy-N-isopropyl-1H-phenalene-1-amine.HCl; melting point 228°-232° C.;

cis 2,3,7,8,9,9a-hexahydro-N,N-dipropyl-1H-phenalene-1-amine.HCl; melting point 162°-163° C.;

cis 2,3,7,8,9,9a-hexahydro-6-methoxy-N,N-dimethyl-1H-phenalene-1-amine.HCl; melting point 258°-260° C.;

cis 2,3,7,8,9,9a-hexahydro-5,6-dimethoxy-N,N-dipropyl-1H-phenalene-1-amine.HCl, melting point 196° C.;

cis 2,3,7,8,9,9a-hexahydro-4,5-dimethoxy-N,N-dimethyl-1H-phenalene-1-amine.HCl;

cis 2,3,7,8,9,9a-hexahydro-5,6-dimethoxy-N-propyl-1H-phenalene-1-amine.HCl, melting point 205°-215° C.

EXAMPLE 3

Preparation: cis 2,3,7,8,9,9a-hexahydro-1H-phenalene-1-methanamine.HCl (a) cis 2,3,7,8,9,9a-hexahydro-1H-phenalene-1-carboxamide 20 g cis 2,3,7,8,9,9a-hexahydro-1H-phenalene-1-carboxylic acid and 8.26 ml thionyl chloride were stirred during one night at room temperature. Subsequently the thionylchloride was evaporated and the residue was dissolved in 80 ml of dry THF. The resultant solution was added dropwise to 106 ml of 25% ammonia, after which the THF was evaporated off. After water had been added to the residue, the resultant precipitate was filtered off, washed with water and dried.

Yield: 18.1 g (91%); melting point 173°-177° C.

(b) Under nitrogen atmosphere 6.42 g of lithium-aluminiumhydride was suspended in 450 ml of dry THF, after which 18.1 g of the compound obtained in (a) was added. The reaction mixture was subsequently boiled for four hours with reflux and then cooled down to +5° C. After 30 ml water had been added to the mixture the deposit was filtered off and the filtrate was concentrated. An equivalent amount of HCl/ethanol was added to the residue and the precipitate obtained was filtered off and recrystallised from ethanol-ether.

Yield: 8.7 g (43%), melting point 230°-239° C. Rf in methanol/acetic acid (98:2)=0.5 on $SiO_2$.

EXAMPLE 4

In an analogous manner the following compounds were produced:

cis 2,3,7,8,9,9a-hexahydro-N-methyl-1H-phenalene-1-methanamine.HCl; melting point 176°-181° C.;

cis 2,3,7,8,9,9a-hexahydro-N-isopropyl-1H-phenalene-1-methanamine.HCl; melting point 182°-185° C.;

cis 2,3,7,8,9,9a-hexahydro-6-methoxy-N-methyl-1H-phenalene-1-methanamine.HCl;

cis 2,3,7,8,9,9a-hexahydro-6-methoxy-N,N-dimethyl-1H-phenalene-1-methanamine.HCl;

cis 2,3,7,8,9,9a-hexahydro-1H-phenalene-3-methanamine;

cis 2,3,7,8,9,9a-hexahydro-N,N-dimethyl-1H-phenalene-1-methanamine.HCl; melting point 243°-244° C.

EXAMPLE 5

Preparation: cis and trans 2,3,7,8,9,9a-hexahydro-5,6-dimethoxy-1H-phenalene-1-amine.HCl A solution of 35.8 ml triethyl amine in 210 ml dry acetone was added dropwise at −5° to −10° C. to a solution of 60 g of 2,3,7,8,9,9a-hexahydro-5,6-dimethoxy-1H-phenalene-1-carboxylic acid in 675 ml acetone (dry), followed by a solution of 28.1 ml chloroformic acid ethyl ester in 210 ml of dry acetone. After stirring for one and a half hours at −5° to −10° C., a solution of 21.75 g sodium azide in 66 ml $H_2O$ was added.

Subsequently stirring was continued for one hour at −5° to −10° C. and then the reaction mixture was poured into ice water and extracted with toluene. The toluene extract was subsequently heated up on a steam bath until no further nitrogen escaped. After toluene was evaporated off the residue was suspended in 362 ml $H_2O$. 412 ml Concentrated HCl was added to this mixture. The mixture was stirred and the resultant deposit was filtered off, dissolved in 2.5 n of NaOH and the solution was extracted with $CH_2Cl_2$. All methylenechloride extracts were dried on $MgSO_4$ and concentrated. An equivalent quantity of HCl/ethanol was added to this residue and the deposit formed was filtered off and recrystallised several times out of ethanol. Yield: 25 g (40%); Rf in methanol/acetic acid (98:2)=0.5 on $SiO_2$. The compound obtained appeared to be the cis-compound. Melting point: 267°-268° C.

The mother liquors obtained during the recrystallisation were concentrated to small volume, after which trifluoro-acetic acid anhydride was added to the solution. The trifluoro-acetyl compound obtained (mixture of cis and trans) was separated chromatographically into the separate cis and trans isomers (silicagel column, running agent: hexane/ethyl acetate (9:1). The cis and trans compounds were subsequently deprotected by means of hydrolysis. Melting point of trans compound as HCl salt: 280°-286° C.

EXAMPLE 6

In a manner analogous to that described in Example 5 the following compounds were prepared:

cis 2,3,7,8,9,9a-hexahydro-1H-phenalene-1-amine.HCl melting point 240°-244° C.;

trans 2,3,7,8,9,9a-hexahydro-1H-phenalene-1-amine.HCl melting point 245°-247° C., cis 2,3,7,8,9,9a-hexahydro-6-methoxy-1H-phenalene-1-amine.HCl, melting point: 264°-266° C.;

cis 1-amino-2,3,7,8,9,9a-hexahydro-1H-phenalene-6-ol.HCl; melting point: 257°-260° C.;

cis 2,3,7,8,9,9a-hexahydro-5-methoxy-1H-phenalene-1-amine.HCl; melting point: 230°-237° C.;

cis 1-amino-2,3,7,8,9,9a-hexahydro-1H-phenalene-5,6-diol.HCl; melting point 261°-262° C.;

cis 2,3,7,8,9,9a-hexahydro-6-methyl-1H-phenalene-1-amine; melting point 220°-229° C.;

cis 2,3,7,8,9,9a-hexahydro-6-chloro-1H-phenalene-1-amine; melting point 280°-290° C.

EXAMPLE 7

Preparation:
4-(2,3,7,8,9,9a-hexahydro-5-methoxy-1H-phenalene-1-ylmethyl)morpholine (a)
4-(2,3,7,8,9,9a-hexahydro-5-methoxy-1H-phenalene-1-yl-carbonyl)morpholine A mixture of 24.6 g cis 2,3,7,8,9,9a-hexahydro-5-methoxy-1H-phenalene-1-carboxylic acid and 8.26 ml thionylchloride was stirred for 20 hours at room temperature. After this the thionylchloride was evaporated off and the residue dissolved in 80 ml dry THF. The resultant solution was added dropwise to a solution of 8.7 ml morpholine in 50 ml THF, after which it was stirred for one hour at room temperature. The mixture was concentrated and the residue stirred up with water. The deposit was filtered off and dried, yield 26.8 g.

(b) Under $N_2$, 6.4 g lithiumaluminiumhydride was suspended in 450 ml dry THF, after which while stirring 26.4 g of the substance obtained in (a) was added. The reaction mixture was further stirred for 3 hours, whereupon 30 ml water was added. The deposit formed was filtered off and the filtrate was concentrated down.

EXAMPLE 8

The following compounds were prepared in a manner corresponding to that described in Example 7:

1-(2,3,7,8,9,9a-hexahydro-6-methoxy-1H-phenalene-1-ylmethyl)-4-methyl-piperazine;

1-(2,3,7,8,9,9a-hexahydro-1H-phenalene-1-ylmethyl)-1H-imidazol, melting point 115°–116° C.;

1-(2,3,7,8,9,9a-hexahydro-1H-phenalene-2-ylmethyl)-1H-imidazol;

2,3,7,8,9,9a-hexahydro-1H-phenalene-N,N-dimethyl-methanamine.HCl, melting point 243°–244° C.

EXAMPLE 9

Preparation:
1-(2,3,7,8,9,9a-hexahydro-1H-phenalene-1-yl)-1H-imidazol 1.14 g Lithiumaluminiumhydride was suspended in 30 ml dry ether, after which a solution of 5.58 g Of 2,3,7,8,9,9a-hexahydro-1H-phenalene-1-on in 10 ml ether was added. The resultant inorganic deposit was filtered off and the filtrate was concentrated. The residue was then dissolved in 10 ml benzne. 2.5 ml of thionylchloride was added to this solution and the reaction mixture was stirred for one hour at room temperature and then concentrated.

The residue was dissolved in 5 ml dry THF and then added dropwise to a suspension which had been prepared as follows: to a suspension of 1.22 g sodiumhydride (60% dispersion in oil) in 5 ml of dry THF a solution of 2.0 g imidazol in 10 ml THF was added, after which the mixture was boiled for 4 hours during reflux. The total reaction mixture was refluxed for a further 6 hours and then concentrated.

The oil-like residue was mixed with ether and then washed with water, dried on magnesium sulphate and once more concentrated.

Yield: 1.7 g (25%) oil. Some crystals could be collected after a while, melting point 173°–174° C. (cis compound).

In an analogous manner the following compound was prepared:

1-(2,3,7,8,9,9a-hexahydro-1H-phenalene-2-yl)-1H-imidazol, melting point 112°–113° C. (trans compound).

EXAMPLE 10

Preparation:
2,3,7,8,9,9a-hexahydro-1H-phenalene-2-amine.HCl (a) 2,3,7,8,9,9a-hexahydro-1H-phenalene-2-on oxim 9.86 g Of 2,3,7,8,9,9a-hexahydro-1H-phenalen-2-on was dissolved in 15 ml pyridine. A solution of 3.8 g hydroxylamine.HCl in 12 ml ethanol/$H_2O$ (1:1) was added to this solution and the mixture was stirred for one hour. The resultant deposit was filtered off, washed off $H_2O$ and dried.

Yield: 9.0 gram.

(b) 9.0 g Of the oxim obtained in (a) was dissolved in 400 ml ethanol. After adding an equivalent quantity of HCl/ethanol and 1.5 g of 5% palladium on carbon, it was hydrogenated in a Parr apparatus for 1.5 hours, after which the catalyst was filtered off and the filtrate was concentrated. The residue was crystallised out from ethanol.

Yield 7.2 g (72%), melting point 308°–311° C.

EXAMPLE 11

Cis N,N-dipropyl-2,3,7,8,9,9a-hexahydro-1H-phenalene-1-amine.HCl 3.78 g Of sodiumborohydride was added to a stirred solution of 24.2 ml propionic acid in 420 ml dry benzene. After no further hydrogen escaped (after about 2 hours) the solution was added to a solution of 3.9 g cis 2,3,7,8,9,9a-hexahydro-1H-phenalene-1-amine in 5 ml benzene. The mixture was boiled for 3 hours under reflux an then cooled down to room temperature. Then 180 ml of 2 n NaOH was added to the mixture, whereupon the resultant layers were separated. The organic layer was dried on magnesium sulphate, when filtered whereafter an equivalent quantity of HCl/ethanol was added to the filtrate. The resulting deposit was filtered off and recrystallised from ethanol/ether (1:1).

Yield: 4.8 g. Melting point 162°–163° C.

In an analogous manner the following compounds were produced:

N,N-diisopropyl-2,3,7,8,9,9a-hexahydro-1H-phenalene-1-amine;

N,N-dipropyl-2,3,7,8,9,9a-hexahydro-5,6-dimethoxy-1H-phenalene-1-amine;

N,N-dipropyl-2,3,7,8,9,9a-hexahydro-4,5-dimethoxy-1H-phenalene-1-amine;

N,N-dipropyl-2,3,7,8,9,9a-hexahydro-5,6-dimethoxy-1H-phenalene-2-amine;

N,N-dipropyl-2,3,7,8,9,9a-hexahydro-6-methoxy-1H-phenalene-1-amine.

EXAMPLE 12

Cis 1-amino-2,3,7,8,9,9a-hexahydro-1H-phenalene-5,6-diol.HCl 8.81 g Cis 2,3,7,8,9,9a-hexahydro-5,6-dimethoxy-1H-phenalene-1-amine.HCl was suspended in 133 ml of 48% HBr, after which the mixture was refluxed for 3 hours under $N_2$ and exclusion of light. After cooling the deposit was filtered off and dried, which resulted in 8.1 g of the desired product as HBr salt.

A column filled with Dowex 50W-X8 (50–100 mesh) was washed with about 500 ml of CH₃OH/H₂O (1:1). 6.0 gram of the HBr salt obtained previously was dissolved in 25 ml CH₃OH/H₂O (1:1). This solution was placed on the column an eluated with CH₃OH/H₂O (1:1) until the eluate was again free from Br. Then elution was carried out with concentrated HCl/H₂O/methanol (2:1:3), the eluate was concentrated and the residue crystallised from methanol/ether.

Yield: 4.4 g (86%), melting point 261°–262° C.

Rf in n-Butanol-acetic acid-water (4:1:1)=0.62 on SiO₂.

EXAMPLE 13

The following compounds are prepared in a manner corresponding to that described in Example 12:
cis 1-dimethylamino-2,3,7,8,9,9a-hexahydro-1H-phenalene-5,6-diol.HCl, melting point: 292°–295° C.;
cis 1-amino-2,3,7,8,9,9a-hexahydro-1H-phenalene-6-ol.HCl, melting point: 257°–260° C.
1-dipropylamino-2,3,7,8,9,9a-hexahydro-1H-phenalene-5,6-diol.HCl, melting point: 228°–235° C.;
2-dipropylamino-2,3,7,8,9,9a-hexahydro-1H-phenalene-5,6-diol;
1-methylamino-2,3,7,8,9,9a-hexahydro-1H-phenalene-5,6-diol.HBr, melting point: 300°–305° C.;
1-dimethylamino-2,3,7,8,9,9a-hexahydro-1H-phenalene-4,5-diol;
cis 1-amino-2,3,7,8,9,9a-hexahydro-1H-phenalene-5-ol.HCl, melting point: 270°–280° C.

EXAMPLE 14

Cis 1-amino-2,3,7,8,9,9a-hexahydro-1H-phenalene-5,6-diol dibenzoate.HCl 4.8 g Of the diol obtained in Example 12 was dissolved in 50 ml of water-free trifluoro acetic acid. After 14 ml benzoyl bromide had been added the mixture was stirred for 48 hours. Then 250 ml of ether was added, the deposit was filtered off and converted into the acetate salt by means of column chromatography using as eluent chloroform-methanol-acetic acid-water (80:20:1:1). The acetate was subsequently converted into the hydrochloride by means of an equivalent quantity of HCl in ethanol. The resulting deposit was filtered off and recrystallised from ethanol-ether.

Yield: 1.2 gram, melting point 219°–220° C.

Rf in chloroform-methanol-acetic acid-water (80:20:1:1)=0.58 on SiO₂.

EXAMPLE 15 trans 2,3,7,8,9,9a-hexahydro-1H-phenalene-2-amine.HCl

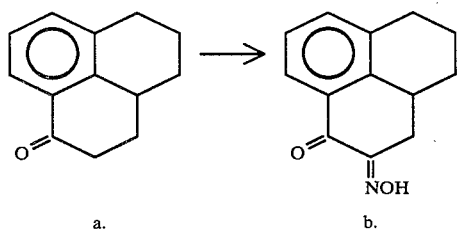

a.     b.

11.7 g potassium tert.butylate was dissolved in 210 ml tert.butanol, and then—under N₂ and while stirring—a solution of 15.4 g (a) in 100 ml dry ether was added dropwise. Then a solution of 11.0 ml isoamyl nitrite in 50 ml t.BuOH was added, whereupon the reaction mixture was refluxed for 3 hours.

After the mixture had cooled down it was concentrated and the residue mixed with 400 ml H₂O and 250 ml ether.

The layers were separated, after which the water layer was washed once more with ether and then acidified with 4 n HCl. Then the acidic water layer was extracted using 3×200 ml ether, whereupon the ether layers were dried on MgSO₄ and concentrated.

Yield (b): 12.0 g (67%); melting point: 137°–139° C.

Rf in toluene-ethanol (8:2)=0.5 on SiO₂.

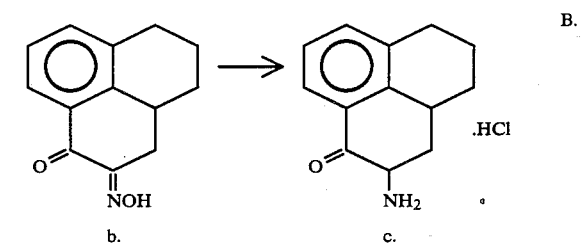

b.     c.

1.0 g Of 10% palladium on carbon was added to 12.0 g (b) dissolved in 250 ml glacial acetic acid. After the theoretical amount of hydrogen had been taken up the catalyst was filtered off, the filtrate was concentrated and the residue was converted into the hydrochloride by means of an equivalent HCl/ethanol. After adding 500 ml dry ether the deposit obtained was filtered off and dried.

Yield: 7.1 g (53%), melting point: 197°–200° C.

Rf in methylene chloride-methanol (9:1)=0.36 on SiO₂.

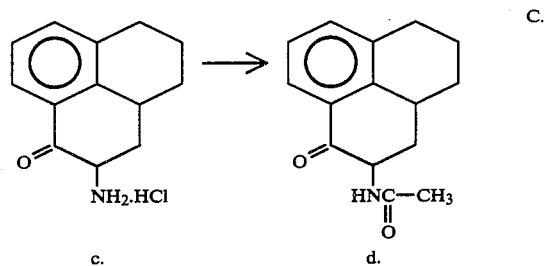

c.     d.

7 g (c) Was added to a mixture of 42 ml pyridine and 21 ml acetic acid anhydride. After 1.5 hours stirring the reaction mixture was poured into water and the deposit obtained was filtered off, washed with water and dried.

Yield (d): 5.7 g (67.5%), melting point 159°–162° C.

Rf in methylenechloride-methanol (97.5:2.5)=on SiO₂.

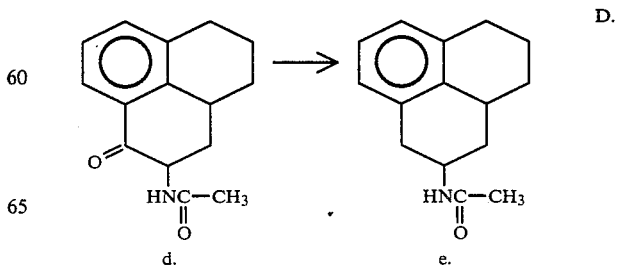

d.     e.

2.7 g Of 10% Pd/c was added to 5.5 g (d) dissolved in 360 ml glacial acetic acid, after which the mixture was hydrolysed. After the theoretical amount of H₂ had been taken up (20 hours) the catalyst was filtered off and the filtrate was concentrated. The residue was crystallised from toluene-petroleumether.

Yield (e): 4.7 g (91%), melting point: 168°-170° C.

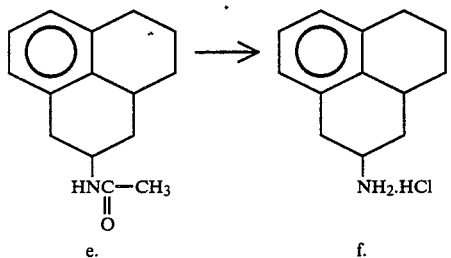

E.

e. f.

4.4 g (e) Suspended in 100 ml of 2 n HCl was boiled for 48 hours under reflux, after which the reaction mixture was concentrated and the residue crystallised out of ethanol-ether.

Yield (f): 3.3 g (77%), melting point 308°-311° C.

EXAMPLE 16

2,3,7,8,9,9a-hexahydro-N,N-dimethyl-1H-phenalene-2-methanamine.HCl

A mixture of 3.7 g 2,3,7,8,9,9a-hexahydro-1H-phenalene-3-on, 2.02 g dimethylamine.HCl, 1.8 g paraformaldehyde and 5 drops of concentrated hydrochloric acid in 25 ml 96% ethanol was boiled under reflux for 1.5 hours. After cooling the reaction mixture was concentrated and the residue suspended in 15 ml of 4 n sodium hydroxide. Then extraction was carried out using 3×10 ml methylene chloride and the organic extracts were collected, dried and evaporated to dryness.

The residue (1.7 g) was dissolved in 45 ml ethanol to which 1 equivalent HCl had been added. After adding 1 g of 10% palladium on carbon, hydrogenation was carried out until the theoretical quantity of hydrogen had been absorbed. The catalyst was then filtered off and the filtrate evaporated to dryness. The residue was crystallised out of ethanol-ether (1:1).

Yield: 1.3 g, melting point: 280°-290° C.

EXAMPLE 17

Cis 2,3,7,8,9,9a-hexahydro-5,6-dimethoxy-N,N-dimethyl-1H-phenalene-1-amine.HCl 2.75 g Sodiumborohydride was added to a solution of 6.8 g cis 2,3,7,8,9,9a-hexahydro-5,6-dimethoxy-1H-phenalene-1-amine (see Example 5) and 11.0 ml of 37% formaldehyde solution in 85 ml acetonitrile. The reaction mixture was stirred for 15 minutes at room temperature, then neutralised with glacial acetic acid and stirred for a further 45 minutes. The reaction mixture was concentrated, after which 110 ml of 2 n KOH was added. The mixture was then extracted with 2×100 ml ether, after which the ether extracts were dried over MgSO₄. After adding an equivalent quantity of HCl in ethanol the resulting precipitate was filtered off and crystallised from ethanol.

Yield: 5.25 g (60%), melting point: 255°-257° C.

Rf in methanol-acetic acid (98:2)=0.1 on SiO₂.

The following compounds were prepared in an analogous manner:

cis 2,3,7,8,9,9a-hexahydro-6-chloro-N,N-dimethyl-1H-phenalene-1-amine.HCl, and cis 2,3,7,8,9,9a-hexahydro-6-methoxy-N,N-dimethyl-1H-phenalene-1-amine.HCl, melting point 258°-260° C.

We claim:

1. A compound of the formula:

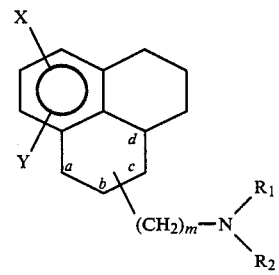

or an acid addition salt thereof wherein the substituent —(CH₂)ₘ—NR₁R₂ is present at one of the positions indicated by a, b or c; X and Y represent hydrogen, (C₁-C₆) alkyl, (C₁-C₆) alkoxy, halogen, hydroxy or benzoyl, R₁ and R₂ represent hydrogen or (C₁-C₆) alkyl and m represents the number 0.

2. A pharmaceutical composition for treatment of CNS disorders which comprises as active ingredient a CNS-effective amount of a compound as defined in claim 1 together with one or more pharmaceutically acceptable carriers.

3. A pharmaceutical composition for treatment of arrhythmic activity which comprises as active ingredient an anti-arrhythmic effective amount of a compound as defined in claim 1 together with one or more pharmaceutically acceptable carriers.

* * * * *